(12) United States Patent
Park et al.

(10) Patent No.: US 8,776,581 B2
(45) Date of Patent: Jul. 15, 2014

(54) BLOOD COLLECTION MODULE FOR MEASURING ALCOHOL CONCENTRATION

(75) Inventors: Kwang Hee Park, Seoul (KR); Ik Hyun Park, Incheon (KR)

(73) Assignee: Elechem Co., Ltd., Incheon (KR)

( * ) Notice: Subject to any disclaimer, the term of this patent is extended or adjusted under 35 U.S.C. 154(b) by 0 days.

(21) Appl. No.: 13/806,707

(22) PCT Filed: Jun. 23, 2011

(86) PCT No.: PCT/KR2011/004593
§ 371 (c)(1),
(2), (4) Date: Dec. 21, 2012

(87) PCT Pub. No.: WO2011/162557
PCT Pub. Date: Dec. 29, 2011

(65) Prior Publication Data
US 2013/0091934 A1    Apr. 18, 2013

(30) Foreign Application Priority Data
Jun. 24, 2010   (KR) .................. 10-2010-0059808

(51) Int. Cl.
G01N 13/00  (2006.01)
(52) U.S. Cl.
USPC ...................................... 73/61.55
(58) Field of Classification Search
USPC ...................................... 73/61.55
See application file for complete search history.

(56) References Cited

U.S. PATENT DOCUMENTS

2002/0177788 A1* 11/2002 Hodges et al. ................ 600/583
2008/0154535 A1   6/2008 Sparks et al.

FOREIGN PATENT DOCUMENTS

| JP | 2008-253455 | 10/2008 |
| KR | 10-2002-0031831 | 5/2002 |
| KR | 10-2003-0011804 | 2/2003 |

OTHER PUBLICATIONS

International Search Report for PCT/KR2011/004593 dated Feb. 16, 2012.

* cited by examiner

*Primary Examiner* — Peter Macchiarolo
*Assistant Examiner* — Alex Devito
(74) *Attorney, Agent, or Firm* — Kile Park Reed & Houtteman PLLC

(57) ABSTRACT

A blood collection module includes a blood collection container that is coupled with a blood alcohol concentration detection device including an alcohol detection sensor having a detection probe that inhales an alcohol gas, and on one surface of which an inserting portion that is inserted by a detection probe of a blood alcohol concentration detection device is formed and on an outer surface of which blood inlet holes through which blood flows in are formed; and an absorption member that is provided in the blood collection container, to thus absorb examinee's blood that is introduced through the blood inlet holes, in which an alcohol gas generated from the blood absorbed by the absorption member is introduced into the alcohol detection sensor through the detection probe.

4 Claims, 6 Drawing Sheets

BLOOD COLLECTION MODULE FOR MEASURING ALCOHOL CONCENTRATION

TECHNICAL FIELD

The present invention relates to a blood collection module for measuring alcohol concentration, and more particularly to a blood collection module for quickly and easily measuring blood alcohol concentration or blood alcohol content (BAC) of a bled unconscious person and judging whether or not he or she is drunk and at the site of car accident.

BACKGROUND ART

Usually, when the police examines whether or not a driver is drunk by using a blood alcohol testing device called a breathalyzer that is the brand name of a breath alcohol testing instrument manufacturer, the driver is made to breathe on an inlet of the blood alcohol testing device, to then enable the blood alcohol testing device to measure alcohol concentration from a breath sample and externally display a result of the measured alcohol concentration. This breath sample type alcohol testing instrument is widely used. The drivers who object to accuracy of the blood alcohol testing device are tested on whether or not they are drunk through blood collection.

However, in the case that a driver becomes unconscious due to occurrence of a car accident, it may not use the breath sample type blood alcohol testing device. In this case, it cannot but inevitably employ a blood sample type alcohol testing instrument that estimates blood alcohol content from a blood sample through blood-gathering. It may consume a considerable amount of time and cost as well as cause cumbersome legal procedures to gather blood of an unconscious person without consent. In addition, since a blood sampling approach through the blood-gathering takes a long time, it may be difficult to accurately measure blood alcohol content (BAC) at the time of the car accident. In other words, since the alcohol absorbed into the body is decomposed at a rate of 0.015%/h, it may be difficult to trust the measured blood alcohol concentration level after a long period of time has elapsed. Therefore, there is the need to quickly and accurately measure blood alcohol content (BAC) from an unconscious person at the time of the car accident.

DISCLOSURE

Technical Problem

In order to solve the above-mentioned problems of conventional art, it is an object of the present invention to provide a blood collection module for legally, quickly, and easily measuring blood alcohol content (BAC) of a bled unconscious person at the time of a car accident.

Technical Solution

To attain the above object of the present invention, according to an aspect of the present invention, there is provided a blood collection module for measuring blood alcohol concentration, the blood collection module comprising:
a blood collection container which includes an inserting portion against which a detection probe of a blood alcohol concentration detection device having an alcohol detection sensor and the detection probe is inserted, and blood inlet holes through which blood is introduced, and an absorption member that is provided in the blood collection container to thus absorb examinee's blood that is introduced through the blood inlet holes,
wherein an alcohol gas generated from the blood absorbed by the absorption member is introduced into the alcohol detection sensor through the detection probe.

According to another aspect of the present invention, the blood collection container further comprises a container cover that covers an upper surface of the blood collection container, wherein the inserting portion is formed on the container cover in the form of a plurality of slits or score lines.

According to still another aspect of the present invention, the blood collection module further comprises an outer container that accommodates the blood collection container, wherein the outer surface of the outer container is coupled with a coupling recess formed in the blood alcohol concentration detection device.

According to yet another aspect of the present invention, a handle that is laterally extended from the container cover is provided for the container cover and a tear-off portion is formed in the handle.

Advantageous Effects

According to the present invention, the blood collection container 10 containing the absorption member 20 that absorbs blood and the blood inlet holes 11 on the surface of it is made to contact blood bled by an unconscious driver who lost consciousness due to a car accident, to thus collect a blood sample, and then the blood collection container 10 that has collected the blood sample is directly inserted into the blood alcohol concentration detection device 60, to thus measure blood alcohol content (BAC). Accordingly, difficulties in collecting a blood sample from an unconscious person who lost consciousness due to a car accident may be solved, and blood alcohol content (BAC) may be quickly measured on the car accident spot to thus obtain a more accurate measurement value, and to thereby quickly and accurately identify car accident details.

In addition, the container cover 30 in which the inserting portion 33 is formed in the form of a plurality of slits or score lines, is coupled on the upper surface of the blood collection container 10, to thus prevent blood from leaking to the outside of the blood collection container 10, and to thereby enable the detection probe 93 of the blood alcohol concentration detection device 60 to be easily inserted into the blood collection container 10 in order for the blood alcohol concentration detection device 60 to easily measure blood alcohol content (BAC).

Also, the blood collection module according to the present invention further comprises the outer container 40 that accommodates the blood collection container 10 stained with blood during collecting blood in which the outer container 40 is coupled with the coupling recess 82 formed in the blood alcohol concentration detection device 60, to thus prevent the blood alcohol concentration detection device 60 and so on from being blood stained.

Meanwhile, the handle 31 that can be torn off is provided in the blood collection container 10 or the container cover 30, to thus improve ease of a blood sampling operation. Further, the handle 31 can be torn off when the blood collection container 10 is kept in storage after being inserted into the blood alcohol concentration detection device 60 or the outer container 40, to thereby enable the blood collection container 10 to be easily inserted into the blood alcohol concentration detection device 60 or the outer container 40 and to accordingly reduce an occupied space for easy storage.

DESCRIPTION OF THE DRAWINGS

The above and other objects and advantages of the invention will become more apparent by describing a preferred embodiment with reference to the accompanying drawings in which.

DETAILED DESCRIPTION OF THE INVENTION

Hereinbelow, a blood collection module according to a preferred embodiment of the present invention will be described with reference to the accompanying drawings.

Figure 1:
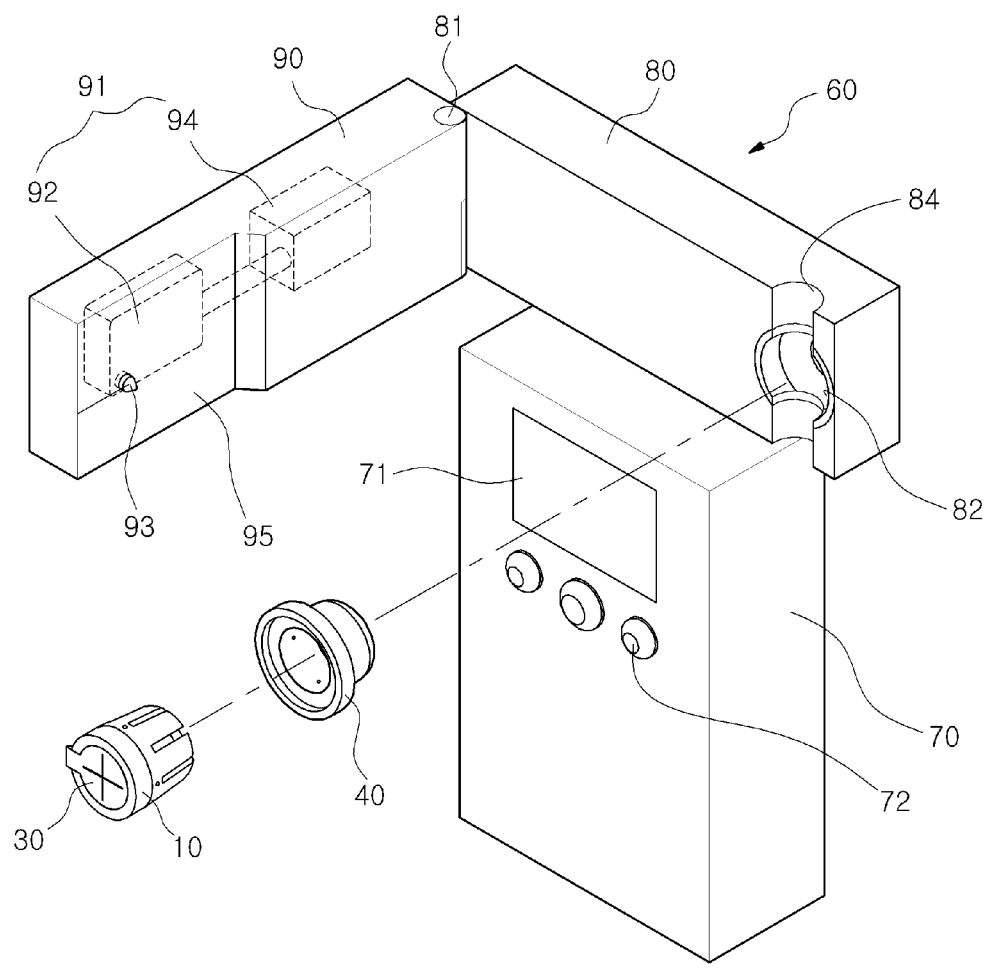
FIG. 1 is a perspective view illustrating a state where a blood collection module according to an embodiment of the present invention is coupled with a blood alcohol concentration detection device.
Figure 2:
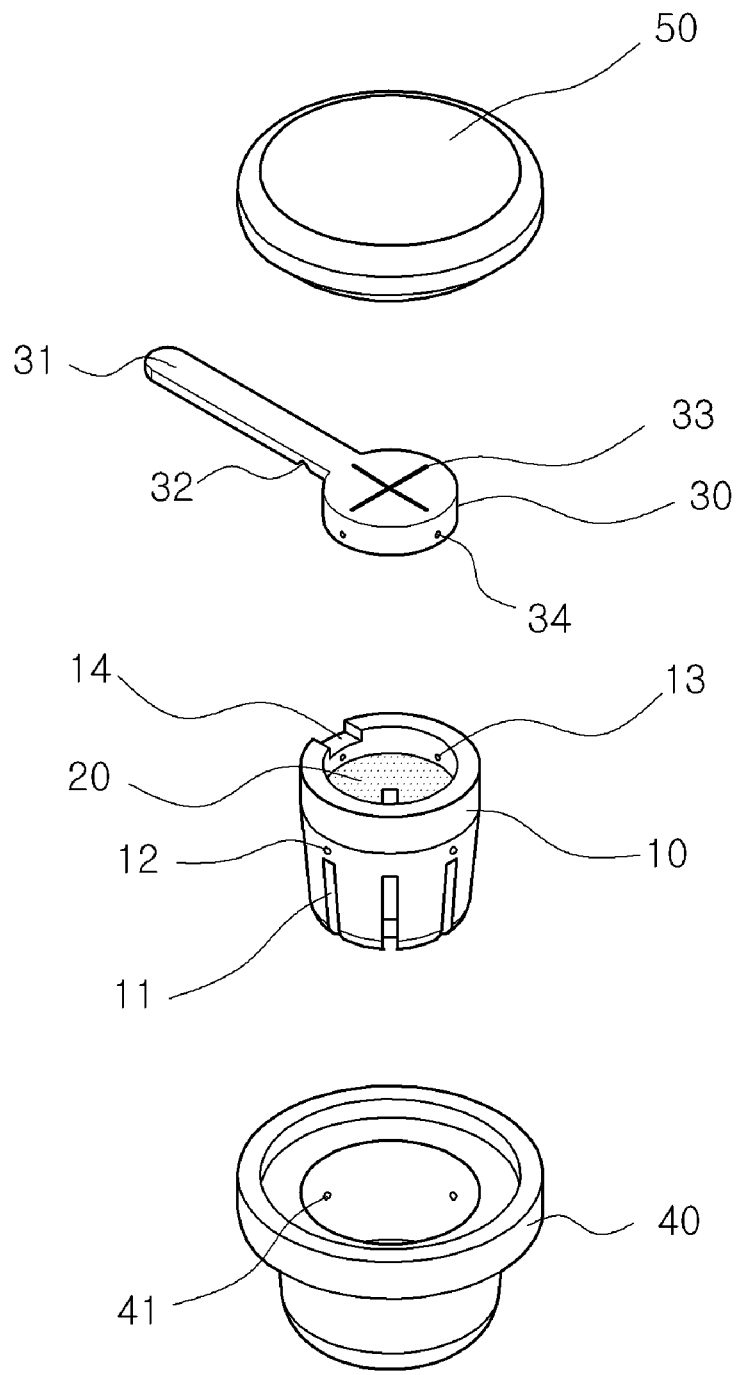
FIG. 2 is an exploded perspective view of a blood collection module according to an embodiment of the present invention.

A blood collection module according to an embodiment of the present invention is coupled with a blood alcohol concentration detection device 60 that measures a blood alcohol content (BAC). As shown in FIG. 1, the blood alcohol concentration detection device 60 includes: a first body 80 on one side surface of which a coupling recess 82 is formed in which a blood collection container 10 of the blood collection module according to an embodiment of the present invention is detachably coupled into the coupling recess 82; a second body 90 that is hinge-coupled with the first body 80 and that is provided with a detection probe 93 and an alcohol detection sensor 91; and a third body 70 that is coupled with the first or second body 80 or 90 and that includes a display 71 on which a blood alcohol content (BAC) detected from the alcohol detection sensor 91 is displayed and a manipulation button unit 72 for measuring the blood alcohol content (BAC).

A built-in heater 83 that heats the inside of the coupling recess 82 is housed in the first body 80, to thus heat the blood collection container 10 that has been coupled into the coupling recess 82 to a set temperature between 30° C. and 40° C., and to thereby place the blood collection container 10 under the same condition as the body temperature. Accordingly, the blood alcohol content (BAC) may be measured more accurately. A sensor module 92 for detecting alcohol concentration in blood and a measuring module 94 for measuring the blood alcohol content (BAC) through a signal detected by the sensor module 92 in the alcohol detection sensor 91, are provided in the second body 90. Meanwhile, a stepped portion 95 that is retracted inwardly in the second body 90, is formed in a region of the second body 90 corresponding to the coupling recess 82 of the first body 80.

The blood collection module for measuring a blood alcohol content (BAC) according to an embodiment of the present invention, includes: a blood collection container 10 on one surface of which an inserting portion 33 that is inserted by the detection probe 93 of the blood alcohol concentration detection device 60 is formed and on an outer surface of which blood inlet holes 11 through which blood flows in are formed; an absorption member 20 that is provided in the inside of the blood collection container 10, to thus absorb blood that is introduced through the blood inlet holes 11; and an outer container 40 that accommodates the blood collection container 10, and that is coupled with the coupling recess 82 formed in the blood alcohol concentration detection device 60.

The blood collection container 10 is a vessel with the top surface open. A fitting groove 14 is formed on one side of the upper portion of the blood collection container 10, and a plurality of blood inlet holes 11 are formed along the circumferential direction on the outer surface of the blood collection container 10. The blood inlet holes 11 are shown in the form of an up-and-down elongate hole, respectively, but are not limited thereto. Any shapes of the blood inlet holes through which blood can be easily absorbed will suffice. In addition, a plurality of holding grooves 13 are formed on the upper portion of the inner surface of the blood collection container 10.

A container cover 30 having a handle 31 in which a tear-off portion 32 is formed is coupled on the upper surface of the blood collection container 10. The handle 31 is inserted into the fitting groove 14. A plurality of stop protrusions 34 that are stopped by the holding grooves 13 of the blood collection container 10, are formed along the circumferential surface of the container cover 30. Accordingly, the container cover 30 is fixedly coupled with the blood collection container 10. In addition, the inserting portion 33 that is inserted by the detection probe 93 of the second body 90 is formed on the container cover 30. The inserting portion 33 may be formed of a variety of shapes and materials, for example, may be formed of a thin film structure that may be easily bored. In addition, the inserting portion 33 may be implemented into a pattern such as '+' or '×' in the form of a plurality of slits or score lines, so that the detection probe 93 can easily penetrate the central portion of the intersection of the inserting portion 33. Therefore, the container cover 30 enables the detection probe 93 to be easily inserted into the blood collection container 10 while preventing the collected blood from leaking.

A plurality of fixing protrusions 12 are formed along the circumferential direction on the outer surface of the upper portion of the blood collection container 10. The container cover 30 is formed separately from the blood collection container 10 in the present embodiment, but alternatively the container cover 30 may be integrally formed with the blood collection container 10.

The absorption member 20 is made of a material that may quickly absorb blood such as a sponge and cotton cloth. Moreover, an absorbent may be added to the absorption member 20 to absorb blood more quickly and strongly. The absorption member 20 is filled in the inside of the blood collection container 10.

Meanwhile, the blood collection container 10 is accommodated in the outer container 40, and a plurality of fixing grooves 41 are formed along the circumferential direction on the upper portion of the inner surface of the outer container 40. Therefore, when the blood collection container 10 is inserted into the outer container 40, the fixing protrusions 12 of the blood collection container 10 are fitted into the fixing grooves 41 of the outer container 40 and thus the blood collection container 10 is fixed to the outer container 40. Accordingly, when blood is collected with the blood collection container 10, the blood stained on the outer surface of the blood collection container 10 is isolated from the outside. As a result, when the blood collection container 10 is inserted into the coupling recess 82 of the blood alcohol concentration detection device 60, the blood alcohol concentration detection device 60 may be prevented from being bloodstained.

Meanwhile, the blood collection container 10 may be coupled with the outer container 40 in a press fit structure. However, in the case that the blood collection container 10 is pressed, blood collected in the blood collection container 10 may be pushed out. Accordingly, it is desirable that the blood collection container 10 is coupled with the outer container 40, in a coupling structure by using the fixing protrusions 12 and the fixing grooves 41. In addition, a cover member 50 that seals the outer container 40 is provided. Accordingly, after the blood alcohol content (BAC) is completely measured through the blood alcohol concentration detection device 60, the blood collection container 10 is put into the inside of the outer container 40 to then seal the outer container 40. Accordingly, blood may be prevented from being deteriorated and smell may be blocked.

Figure 3:
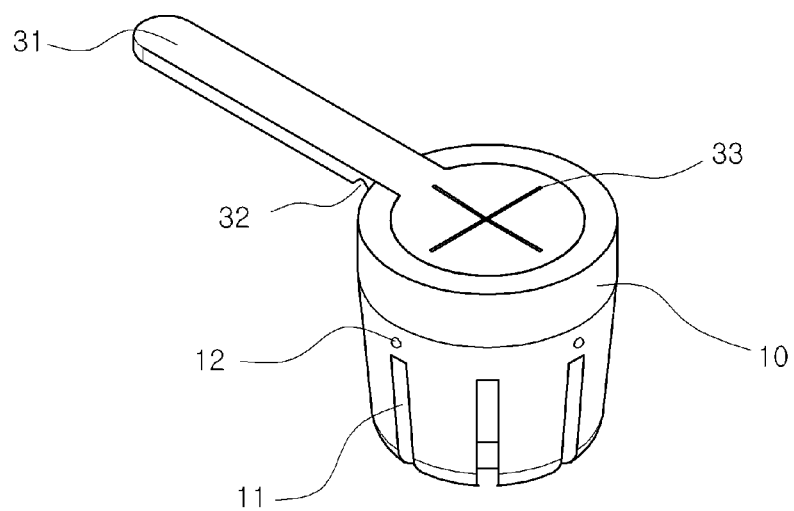
FIG. 3 is an assembled perspective view illustrating essential parts of the blood collection module according to the embodiment of the present invention.
Figure 4:
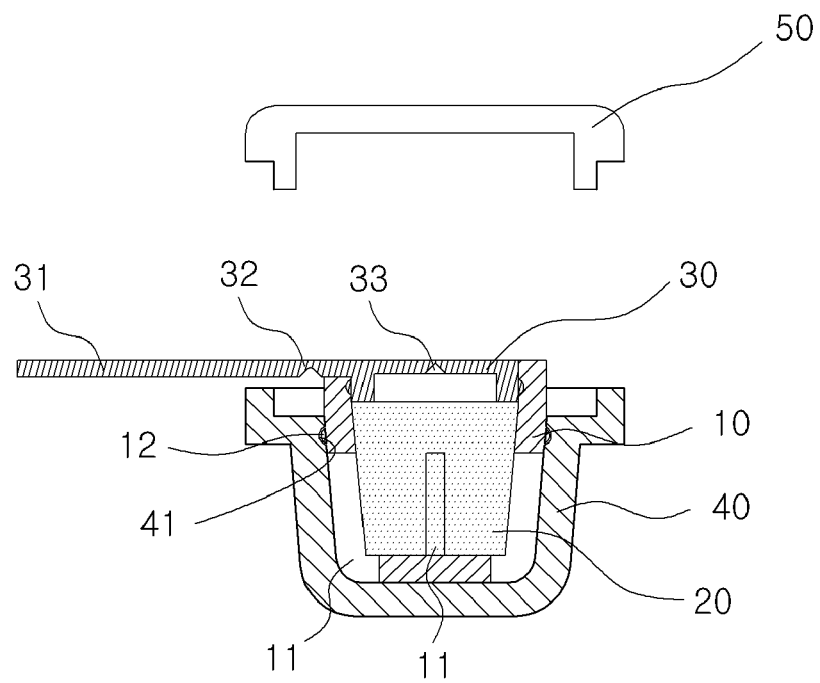
FIG. 4 is a side cross-sectional view of the blood collection module according to the embodiment of the present invention.
Figure 5:
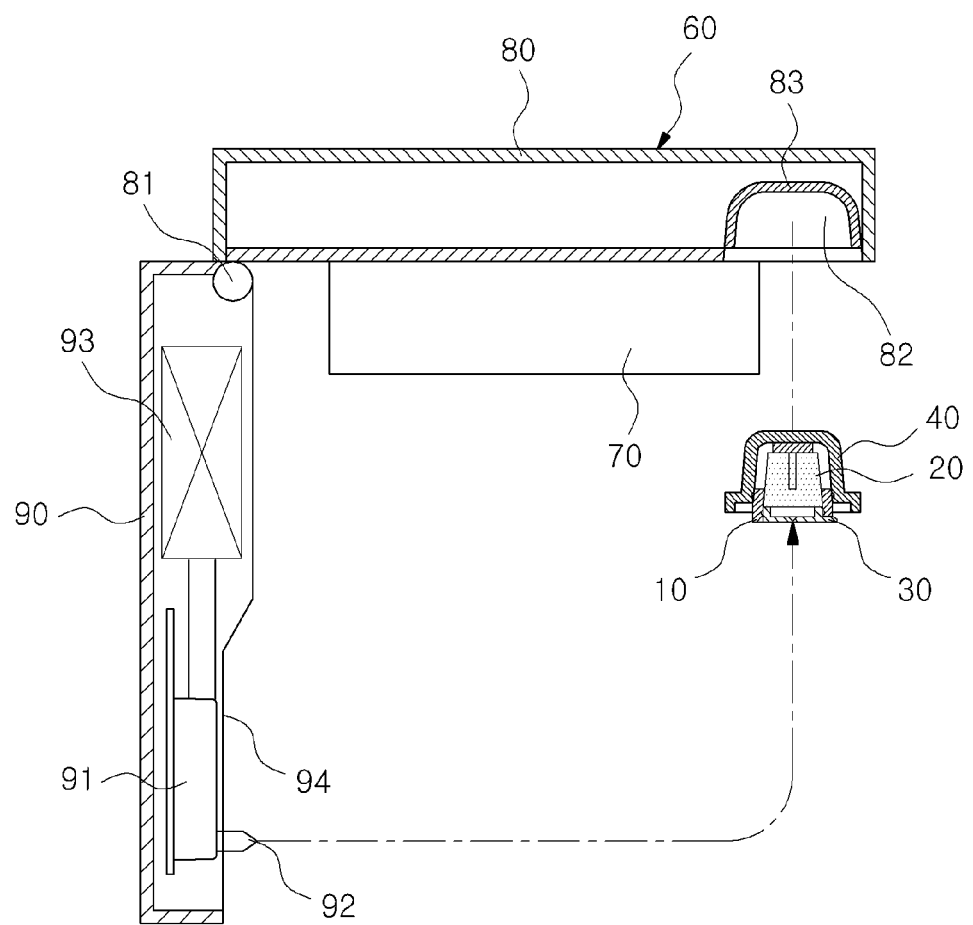
FIG. 5 is a top cross-sectional view illustrating a state where a blood collection module according to an embodiment of the present invention is being coupled with a blood alcohol concentration detection device.
Figure 6:
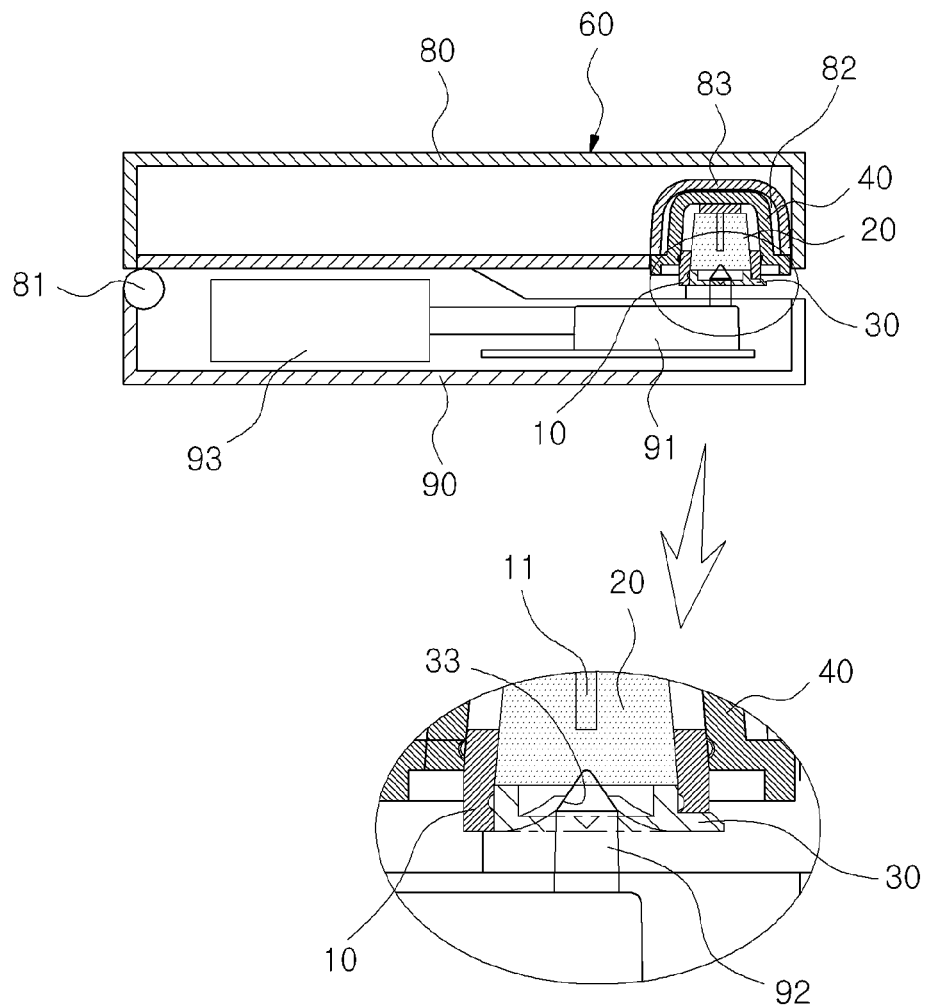
FIG. 6 is a top cross-sectional view illustrating a state where a blood collection module according to an embodiment of the present invention has been coupled with a blood alcohol concentration detection device.

Operations of collecting a blood sample and measuring a blood alcohol content (BAC) through the blood collection module having the above-described structure according to an embodiment of the present invention, will be described below. Referring to FIG. 3 showing a state where the outer container 40 and the cover member 50 are removed from the blood collection container 10, first an examiner holds the handle 31 of the container cover 30 and makes the blood collection container 10 contact blood bled by the examinee, then the blood may be introduced into the inside of the blood collection container 10 through the blood inlet holes 11 formed in the blood collection container 10. The introduced blood is absorbed in the absorption member 20 filled in the blood collection container 10. In addition, in the case that the outer surface of the blood collection container 10 is bloodstained, the examiner or the blood alcohol concentration detection device 60 may be bloodstained. Thus, to prevent this, the blood collection container 10 is put into the outer container 40 and then the handle 31 of the container cover 30 is torn off at the tear-off portion 32 to be removed from the container cover 30.

Thereafter, the outer container 40 into which the blood collection container 10 has been inserted is fitted into the coupling recess 82 of the first body 80, and then the second body 90 is rotated toward the first body 80. Accordingly, the detection probe 93 of the second body 90 penetrates the inserting portion 33 of the container cover 30 attached on the blood collection container 10 to then be advanced into the blood collection container 10. Then, blood contained in the blood collection container 10 is heated by the heater 83 to thus generate an alcohol gas. Then, the generated alcohol gas is introduced into the alcohol detection sensor 91 through the detection probe 93, to thus make it possible to measure a blood alcohol content (BAC) in the measuring module 93 and to display the measurement value on the display 71.

As described above, according to the present invention, blood bled by an unconscious person who lost consciousness on an accident spot may be legally and quickly collected through the blood collection container 10, without passing through a complicated procedure for collecting a blood sample with no consent of the unconscious person. In addition, blood alcohol content (BAC) may be measured directly from the blood sample through the blood alcohol concentration detection device 60, to thus reduce an error due to a delay in time and to thereby measure accurate blood alcohol content (BAC). Meanwhile, the blood alcohol concentration detection device 60 that has been described in the present embodiment is only an example, and alternatively various shapes of blood alcohol concentration detection devices having a detection probe that is inserted into the blood collection container 10 may be applied in the present invention.

As described above, the present invention has been described with respect to particularly preferred embodiments. However, the present invention is not limited to the above embodiments, and it is possible for one who has an ordinary skill in the art to make various modifications and variations, without departing off the spirit of the present invention. Thus, the protective scope of the present invention is not defined within the detailed description thereof but is defined by the claims to be described later and the technical spirit of the present invention.

The invention claimed is:

1. A blood collection module used for measuring blood alcohol concentration by use of the blood alcohol concentration detection device having an alcohol detection sensor and a detection probe, the blood collection module comprising:
   a blood collection container comprising a cup including a peripheral sidewall and a lower surface and having an opening on the upper surface and blood inlet passages through at least one of said side wall and lower surface,
   a container cup cover placed on top of said blood collection container cup and having an inserting portion through said container cup cover in the form of at least one of plural slits and score lines against which the detection probe of the blood alcohol concentration detection device is operable to be inserted through said container cup cover,
   an absorption member that is provided in the blood collection container cup to absorb an examinee's blood that is introduced through the blood inlet passages,
   wherein an alcohol gas generated from the blood absorbed in the absorption member is introduced into the alcohol detection sensor through the detection probe.

2. The blood collection module according to claim 1, wherein a handle that is laterally extended from the container cup cover is provided for the container cover and a tear-off portion is formed in the handle.

3. The blood collection module according to claim 1, wherein the blood collection module further comprises an outer container cup that accommodates the blood collection container cup, wherein the outer surface of the outer container is coupled with a coupling recess formed in the blood alcohol concentration detection device.

4. The blood collection module according to claim 1 and further comprising a heating element operable to surround said outer container cup and heat a blood sample within said blood collection container to a temperature between 30° C. and 40° C. to thereby place the collection container cup under a similar temperature condition as human body temperature.

* * * * *